United States Patent
Baxi et al.

(10) Patent No.: US 10,959,633 B2
(45) Date of Patent: Mar. 30, 2021

(54) WEARABLE SENSING PATCH TECHNOLOGIES

(71) Applicant: Intel Corporation, Santa Clara, CA (US)

(72) Inventors: Amit Baxi, Thane West (IN); Adel Elsherbini, Chandler, AZ (US); Vincent Mageshkumar, Navi Mumbai (IN); Sasha Oster, Chandler, AZ (US); Aleksandar Aleksov, Chandler, AZ (US); Feras Eid, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 540 days.

(21) Appl. No.: 15/837,508

(22) Filed: Dec. 11, 2017

(65) Prior Publication Data

US 2019/0038170 A1    Feb. 7, 2019

(51) Int. Cl.
*A61B 5/0408* (2006.01)
*A61B 5/01* (2006.01)
*A61B 5/026* (2006.01)
*A61B 5/0205* (2006.01)
*A61B 5/021* (2006.01)
(Continued)

(52) U.S. Cl.
CPC ............ *A61B 5/04085* (2013.01); *A61B 5/01* (2013.01); *A61B 5/0205* (2013.01); *A61B 5/0261* (2013.01); *A61B 5/021* (2013.01); *A61B 5/0816* (2013.01); *A61B 5/6801* (2013.01);
(Continued)

(58) Field of Classification Search
CPC ..... A61B 5/04085; A61B 5/01; A61B 5/0205; A61B 5/0261; A61B 5/021; A61B 5/0861; A61B 5/6833; A61B 5/04087; A61B 5/6802; A61B 5/6801; A61B 2560/0412; A61B 5/6832

See application file for complete search history.

(56) References Cited

U.S. PATENT DOCUMENTS

| | | | | |
|---|---|---|---|---|
| 5,660,177 A | * | 8/1997 | Faupel | ..................... A61B 5/04 600/382 |
| 2012/0089037 A1 | * | 4/2012 | Bishay | ................. A61B 5/6833 600/509 |

(Continued)

OTHER PUBLICATIONS

CardioleafULTRA Product Video HD. Youtube, published by Clearbridge Vitalsigns, Nov. 7, 2012, https://www.youtube.com/watch?v=IQ7vl-cNbq8.

(Continued)

*Primary Examiner* — Eun Hwa Kim
*Assistant Examiner* — Rachel A. Vierra
(74) *Attorney, Agent, or Firm* — Alliance IP, LLC

(57) ABSTRACT

Sensing patch systems are disclosed herein. A sensing patch system includes a flexible substrate and a sensor node. The flexible substrate includes one or more substrate sensors configured to provide sensor data, one or more substrate conductors electrically coupled to a corresponding substrate sensor to conduct the sensor data provided by the corresponding substrate sensor, and a node interface. The sensor node includes a substrate interface configured to receive the node interface of the flexible substrate. The sensor node is configured to receive the sensor data provided by the substrate sensors, process the sensor data, and communicate the processed sensor data to a remote device.

11 Claims, 10 Drawing Sheets

(51) Int. Cl.
    *A61B 5/08* (2006.01)
    *A61B 5/00* (2006.01)
(52) U.S. Cl.
    CPC .......... *A61B 5/6802* (2013.01); *A61B 5/6832* (2013.01); *A61B 5/6833* (2013.01)

(56) References Cited

U.S. PATENT DOCUMENTS

2015/0087950 A1* 3/2015 Felix ................ A61B 5/04085
                                                              600/382
2016/0296170 A1* 10/2016 Putila ................ A61B 5/02444

OTHER PUBLICATIONS

Medtronic Cardiac Diagnostics and Monitoring for Healthcare Professionals. "SEEQ Mobile Cardiac Telemetry System." http://www.medtronicdiagnostics.com/us/cardiac-monitors/seeq-mct-system/index.htm, as captured by the Wayback Machine on Feb. 12, 2018, and accessed on Jul. 27, 2020.

Imec. "Health Patch." http://www.imec-int.com/drupal/sites/default/files/2016-12/Imec%20Health%20Patch.pdf. Accessed Jul. 27, 2020.

Dexcom Continuous Glucose Monitoring. "What is (CGM) Continuous Glucose Monitoring?" https://www.dexcom.com/continuous-glucose-monitoring. Accessed Jul. 27, 2020.

Monica Healthcare. "Novii Wireless Patch System." http://www.monicahealthcare.com/products/labour-and-delivery/monica-novii-wireless-patch-system. Accessed Jul. 27, 2020.

* cited by examiner

WEARABLE SENSING PATCH TECHNOLOGIES

BACKGROUND

Wearable systems are used in some applications to monitor human biological functions. Those systems may incorporate components capable of flexing to establish and/or maintain contact with subjects when the subjects are at rest or performing physical activity. Some wearable systems are customized to a particular application and designed for one-time usage. Because the components of such systems are typically discarded after a single use, those systems may be more costly, and provide less modularity, than systems that incorporate one or more components designed for repeated usage in one or more applications.

Wearable systems that incorporate reusable components are not without drawbacks. Such systems may utilize connectors with constructions that limit the ability of the connectors to stretch, which may be undesirable for application to subject areas where frequent movement occurs. Undesirable fabrication complexity may also be attendant to integration of those connectors with other components of those systems. Finally, because the connectors are often provided on disposal components, the connectors may undesirably increase the cost of those components and each system as a whole.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

Figure 1:
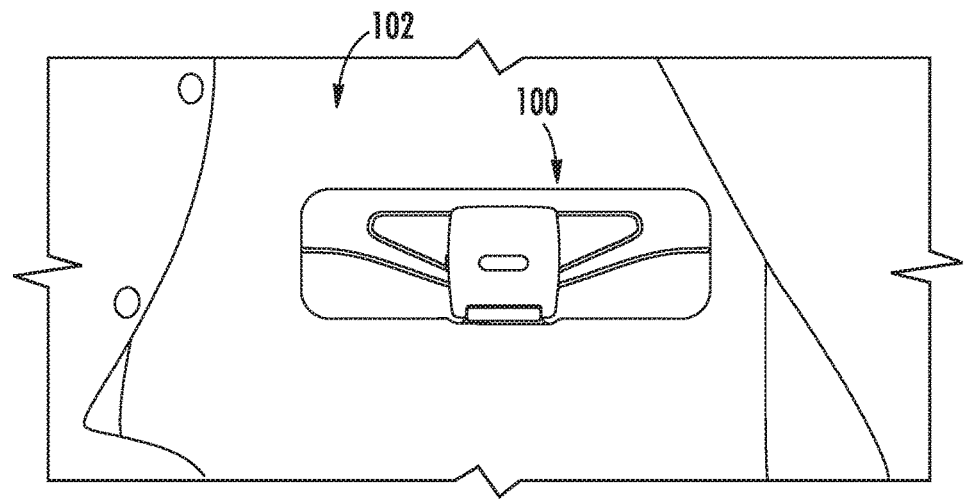
FIG. 1 is a perspective view of at least one embodiment of a sensing patch system that is applied to a human subject.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C).

Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a sensing patch system 100 is applied to a human subject 102 to sense physiological characteristics of the subject 102. Those physiological characteristics may include, but are not limited to, respiratory activity, cardiac activity, motor neuron activity, blood glucose levels, skin temperature, blood pressure, and/or activity associated with other bodily features. As discussed below, the illustrative sensing patch system 100 may be embodied as a wearable technology capable of sensing physiological characteristics of the subject 102 when the subject 102 is at rest or performing physical activity.

In other embodiments, the sensing patch system 100 may be applied to a non-human subject. The sensing patch system 100 may be applied to furnishings or appliances, for example. In such examples, the sensing patch system 100 may be embodied as, or otherwise included in, a tension, compression, and/or pressure sensing device.

Figure 2:
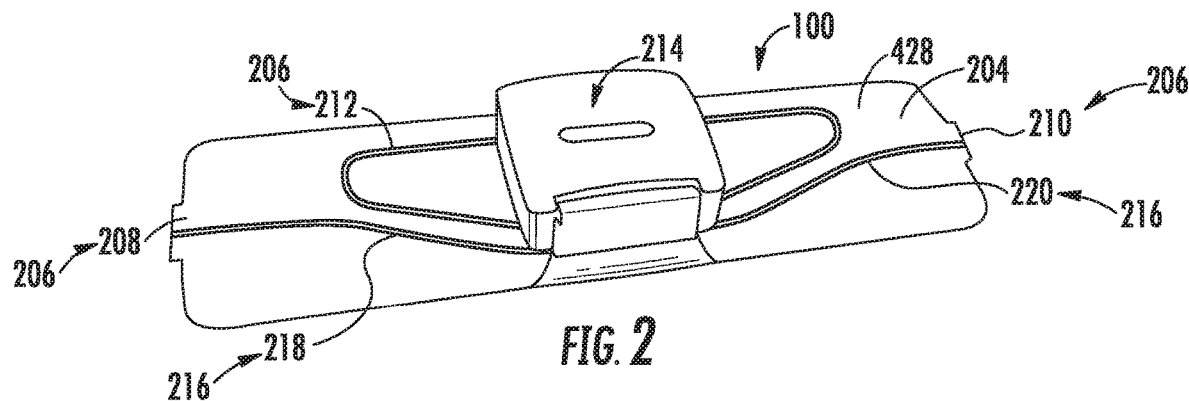
FIG. 2 is a perspective view of one side of the sensing patch system of FIG. 1 that faces away from the subject when the sensing patch system is applied to the subject.

Referring now to FIG. 2, the illustrative patch sensing system 100 includes a flexible substrate 204 and a sensor node 214. The flexible substrate 204 is illustratively embodied as any device capable of directly contacting the subject 102, flexing and/or stretching with the skin of the subject 102 in response to movement of the subject 102, and providing data indicative of one or more physiological characteristics of the subject 102 to the sensor node 214. The sensor node 214 is illustratively embodied as any device capable of directly contacting the subject 102, receiving the data provided by the flexible substrate 204, processing the data, and communicating the processed data to a remote device.

Figure 4:
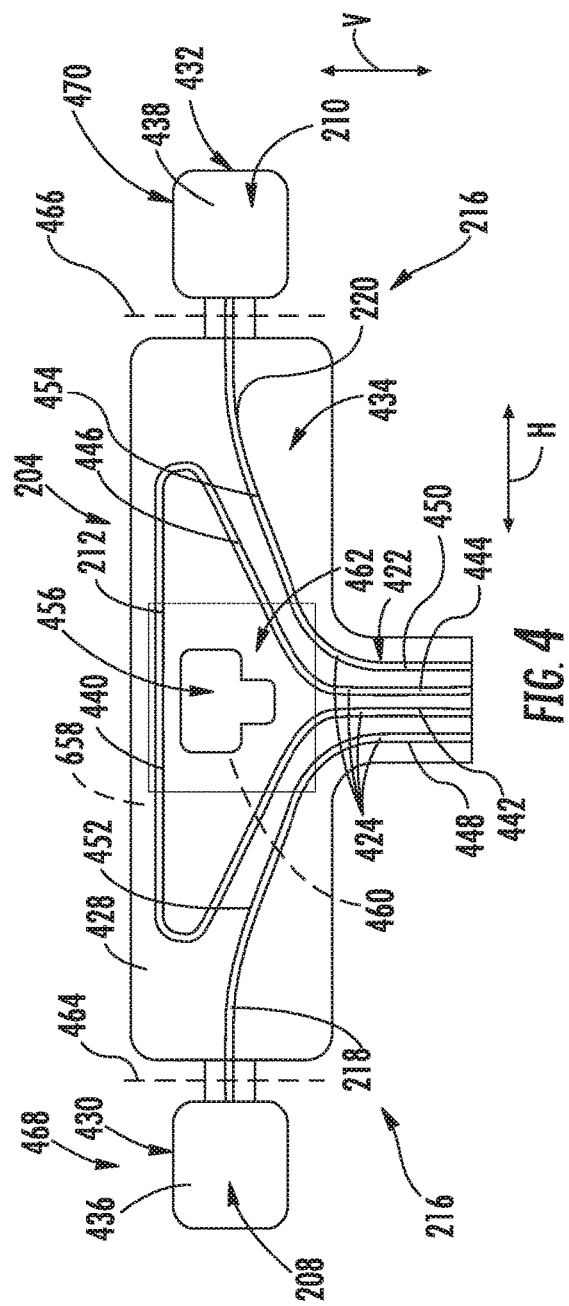
FIG. 4 is an elevation view of one side of a flexible substrate of the sensing patch system of FIG. 1 with sensor pads of the flexible substrate in fully unfolded positions.

The illustrative flexible substrate 204 includes substrate sensors 206, substrate conductors 216, and a node interface 422 as shown in FIGS. 2 and 4. The substrate sensors 206 are illustratively embodied as sensors or any other devices capable of sensing physiological characteristics of the subject 102 and providing sensor data indicative of the sensed physiological characteristics. Each of the substrate conductors 216 is electrically coupled to a corresponding substrate sensor 206, and as such, each substrate conductor 216 is illustratively embodied as an electrical conductor or any other device capable of conducting the sensor data provided by the corresponding substrate sensor 206. Each of the substrate conductors 216 includes a terminal end 424. The terminal end 424 is located at the node interface 422, and the node interface 422 is illustratively embodied as any interface capable of interacting with the sensor node 214 to establish electrical contact between the flexible substrate 204 and the sensor node 214.

Figure 9:
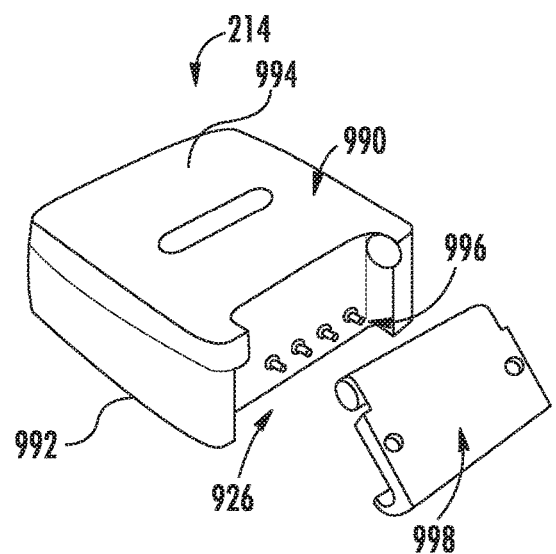
FIG. 9 is an exploded perspective view of a sensor node of the sensing patch system of FIG. 1 with one side facing upward.
Figure 17:
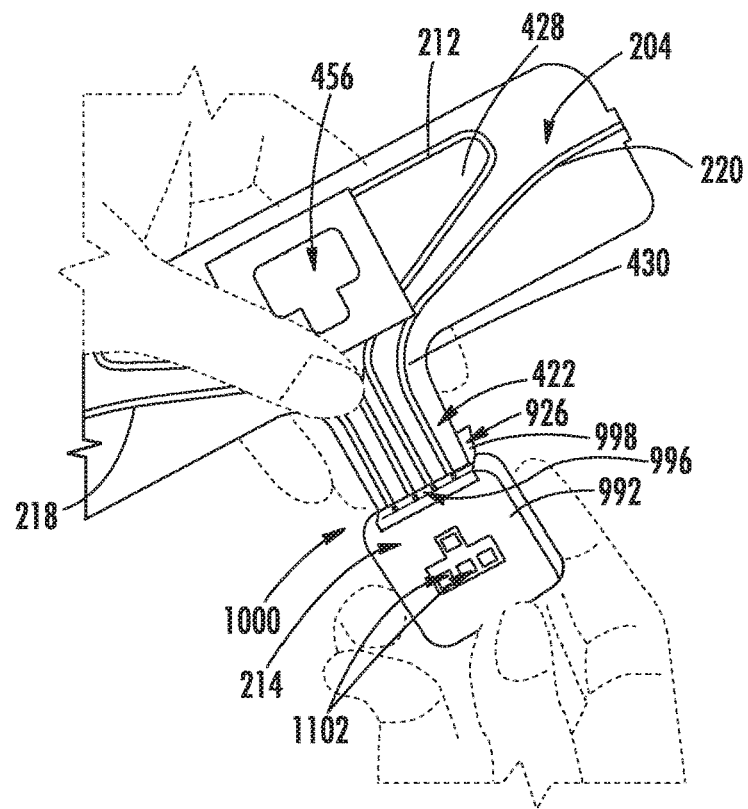
FIG. 17 is a perspective view of the sensing patch system with the node interface received by the substrate interface when assembling the sensing patch system by the method of FIG. 15.
Figure 18:
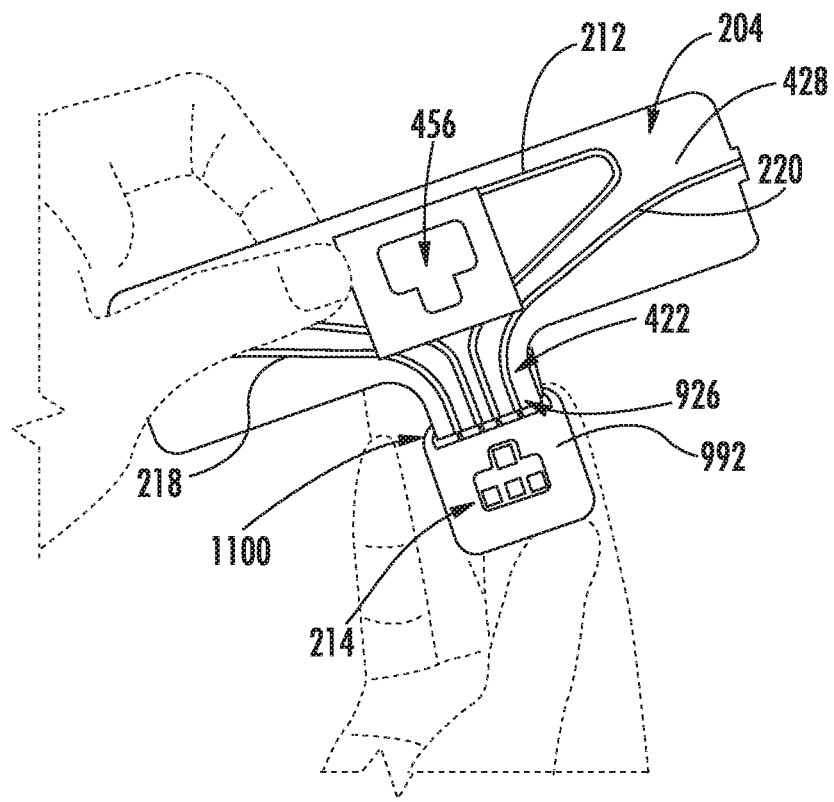
FIG. 18 is a perspective view of the sensing patch system with the node interface received by the substrate interface to secure electrical contact between the flexible substrate and the sensor node when assembling the sensing patch system by the method of FIG. 15.

The illustrative sensor node 214 includes a substrate interface 926 as shown in FIG. 9. The substrate interface 926 is illustratively embodied as any interface capable of receiving the node interface 422 of the flexible substrate 204. When the node interface 422 is received by the substrate interface 926 as shown in FIGS. 17 and 18, the sensor node 214 establishes electrical contact with each of the terminal ends 424 of the substrate conductors 216.

The node interface 422 of the flexible substrate 204 illustratively mates directly with the substrate interface 926 of the sensor node 214 to establish electrical contact between the flexible substrate 204 and the sensor node 214 when the node interface 424 is received by the substrate interface 926. As a result, the node sensor 214 establishes electrical contact with the flexible substrate 204 without interaction with a connector separate from the substrate conductors 216 that is integrated into, or otherwise coupled to, the flexible substrate 204. Exclusion of such a connector may reduce the cost and fabrication complexity of the illustrative sensing patch system 100 compared to other configurations that employ the connector or a similar connective feature.

Figure 3:
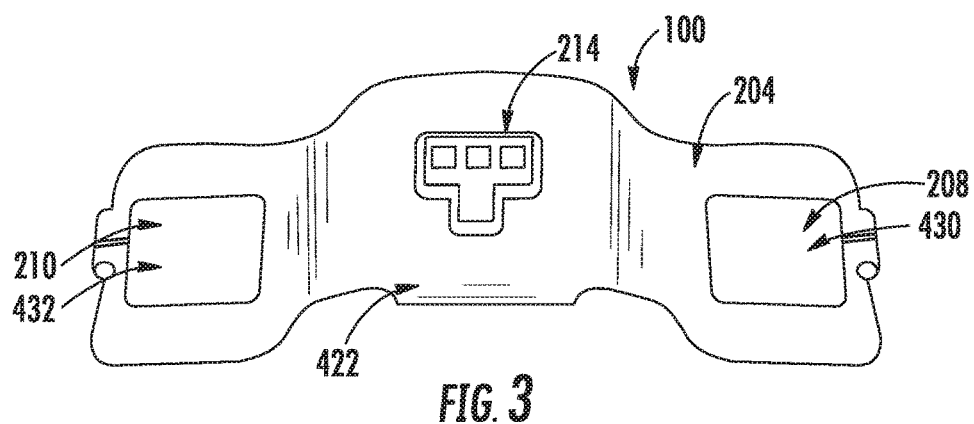
FIG. 3 is a perspective view of another side of the sensing patch system of FIG. 1 that faces toward the subject when the sensing patch system is applied to the subject.

Referring now to FIG. 3, when the sensing patch system 100 is assembled, the sensor node 214 is illustratively arranged to extend through the flexible substrate 204. More specifically, as discussed below, the sensor node 214 of the assembled sensing patch system 100 protrudes through a cutout 456 formed in the flexible substrate 204. Thus, when the sensing patch system 100 is applied to the subject 102, both the flexible substrate 204 and the sensor node 214 directly contact the subject 102. As discussed in more detail below, direct contact between the sensor node 214 and the subject 102 enables the sensor node 214 to sense physiological characteristics of the subject 102 and provide node sensor data indicative of the sensed physiological characteristics. Because sensing capabilities are provided by the sensor node 214, which is configured for repeated usage in each of multiple applications as discussed below, sensing elements of the node sensor 214 are configured for such usage. Repeated usage of those sensing elements may reduce the cost and enhance the functionality of the illustrative sensing patch system 100 compared to other configurations that provide sensors only on elements discarded after one-time usage.

Referring now to FIG. 4, an illustrative surface 428 of the flexible substrate 204 that faces away from the subject 102 when the sensing patch system 100 is applied to the subject 102 is shown. The surface 428 illustratively includes a sensor pad 430, a sensor pad 432, and a body section 434 extending between the sensor pads 430, 432. The sensor pads 430, 432 are interconnected with the body section 434 opposite one another. A substrate sensor 208 is formed on the sensor pad 430, a substrate sensor 210 is formed on the sensor pad 432, and a substrate sensor 212 is formed on the body section 434. The node interface 422 extends downwardly away from the body section 434, and the substrate conductors 216 extend over the body section 434 to the terminal ends 424 located at the node interface 422.

The substrate sensor 208 illustratively includes an electrode 436 formed on the sensor pad 430. In the illustrative embodiment, the electrode 436 is embodied as, or otherwise includes, an electrocardiogram sensor configured to sense cardiac activity of the subject 102. In other embodiments, however, the electrode 436 may be embodied as, or otherwise include, another sensor configured to sense another physiological characteristic of the subject 102. In any case, the electrode 436 is formed from conductive ink as discussed below.

The substrate sensor 210 illustratively includes an electrode 438 formed on the sensor pad 432. In the illustrative embodiment, the electrode 438 is embodied as, or otherwise includes, an electrocardiogram sensor configured to sense cardiac activity of the subject 102. In other embodiments, however, the electrode 438 may be embodied as, or otherwise include, another sensor configured to sense another physiological characteristic of the subject 102. In any case, the electrode 438 is formed from conductive ink as discussed below.

The substrate sensor 212 illustratively includes an electrical trace 440 formed on the body section 434 that has terminal ends 442, 444 located at the node interface 422 and a generally triangular-shaped portion 446 coupled to the ends 442, 444 as shown in FIG. 4. As discussed below, the electrical trace 440 is formed from conductive ink. It should be appreciated, however, that the electrical trace 440 may be formed from other suitable materials, such as, for example, stretchable non-conductive fabrics and conductive fabric traces. In the illustrative embodiment, the substrate sensor 212 is embodied as, or otherwise includes, a breathing sensor configured to provide respirational data indicative of respirational activity of the subject 102 and conduct the respirational data to the node interface 422 (i.e., in the form of an electrical signal). The body section 434 is configured to stretch in a horizontal direction H in response to movement of the subject 102 (e.g., stretching of the skin of the subject 102) such that the respirational data provided by the substrate sensor 212 varies accordingly, as discussed below. In other embodiments, the substrate sensor 212 may be embodied as, or otherwise include, another sensor configured to provide data indicative of another physiological characteristic.

In the illustrative embodiment, the flexible substrate 204 includes two substrate sensors 208, 210 formed on respective sensor pads 430, 432 and one substrate sensor 212 formed on the body section 434. The illustrative flexible substrate 204 therefore includes three substrate sensors 208, 210, 212. In other embodiments, however, the flexible substrate 204 may include another suitable number of substrate sensor(s) other than three. In such embodiments, the substrate sensor(s) may be formed on other suitable location(s) of the surface 428 other than the pads 430, 432 and the body section 434.

An illustrative substrate conductor 218 is electrically coupled to the substrate sensor 208 to conduct data provided by the electrode 436 to a terminal end 448 of the conductor 218 located on the node interface 422. Consequently, the substrate conductor 218 extends from the sensor pad 430 over the body section 434 to the node interface 422 as shown in FIG. 4. As discussed in more detail below, the substrate conductor 218 is illustratively embodied as, or otherwise includes, an electrical trace formed from conductive ink.

An illustrative substrate conductor 220 is electrically coupled to the substrate sensor 210 to conduct data provided by the electrode 438 to a terminal end 450 of the conductor 220 located on the node interface 422 as shown in FIG. 4. Consequently, the substrate conductor 220 extends from the sensor pad 432 over the body section 434 to the node interface 422 as shown in FIG. 4. As discussed in more detail below, the substrate conductor 220 is illustratively embodied as, or otherwise includes, an electrical trace formed from conductive ink.

The substrate conductors 218, 220 are illustratively formed on the surface 428 of the flexible substrate 204 such that the conductors 218, 220 face away from the subject 102 when the sensing patch system 100 is applied to the subject 102. Thus, the substrate conductors 218, 220 are not in contact with the skin of the subject 102 when the system 100 is applied thereto. Formation of the conductors 218, 220 on the surface 428 consequently reduces exposure of the conductors 218, 220 to heat and/or moisture from the skin of the subject 102. As might otherwise be the case in configurations in which conductors contact a subject's skin, the conductors 218, 220 are formed substantially without electrically insulative layers. The conductors 218, 220 therefore include respective portions 452, 454 that are non-insulated. It should be appreciated, however, that the conductors 218, 220 may be formed with electrically insulative layers for protection from environmental conditions, such as insulative layers used to waterproof the conductors 218, 220, for example.

In the illustrative embodiment, the flexible substrate 204 includes two substrate conductors 218, 220 corresponding to the respective substrate sensors 208, 210. In other embodiments, however, the flexible substrate 204 may include another suitable number of substrate conductor(s) other than two depending on the number of corresponding substrate sensors.

The terminal end 448 of the conductor 218, the terminal end 450 of the conductor 220, and the terminal ends 442, 444 of the substrate sensor 212 are illustratively located at the node interface 422. The terminal ends 442, 444, 448, 450 extend parallel to one another downwardly away from the body section 434. The terminal ends 442, 444 are illustratively arranged between the terminal ends 448, 450. In other embodiments, however, the terminal ends 442, 444, 448, 450 may have another suitable arrangement at the node interface 422.

Referring still to FIG. 4, the flexible substrate 204 illustratively includes the cutout 456 that extends through the body section 434 of the surface 428 and a surface 658 facing away from the surface 428. The cutout 456 is arranged relative to the electrical trace 440 of the substrate sensor 212 such that the generally triangular-shaped portion 446 extends around the cutout 456. As discussed in more detail below, the cutout 456 is configured to receive the sensor node 214 such that the sensor node 214 directly contacts the subject 102 when the sensing patch system 100 is applied to the subject 102. In addition, as further discussed below, the sensor node 214 contacts the surface 428 when received by the cutout 456.

The illustrative flexible substrate 204 also includes an adhesive region 460 formed on the body section 434 of the surface 428. A liner 462 covers the adhesive region 460 to permit selective exposure of the adhesive region 460 beneath the liner 462. The adhesive region 460 is arranged relative to the cutout 456 such that the region 460 extends around the cutout 456. When the liner 462 is removed and the sensor node 214 is received by the cutout 456, as discussed in more detail below, the sensor node 214 adheres to the adhesive region 460. After adhering to the adhesive region 460, the sensor node 214 is removable from the region 460 as discussed below.

Referring now to FIGS. 4-7, each of the illustrative sensor pads 430, 432 are foldable relative to the body section 434. More specifically, the sensor pads 430, 432 are foldable about respective axes 464, 466 relative to the body section 434 between fully unfolded positions 468, 470 and fully folded positions 672, 674. In the illustrative embodiment, the sensor pads 430, 432 are configured to fold away from the body section 434 of the surface 428 and toward the surface 658 as the pads 430, 432 move from the fully unfolded positions 468, 470 toward the fully folded positions 672, 674.

In the illustrative fully unfolded positions 468, 470 of the respective sensor pads 430, 432, the sensor pads 430, 432 face in the same direction as the body section 434 of the surface 428 as shown in FIG. 4. As such, the sensor pads 430, 432 face away from the surface 658 in the fully unfolded positions 468, 470.

Figure 5:
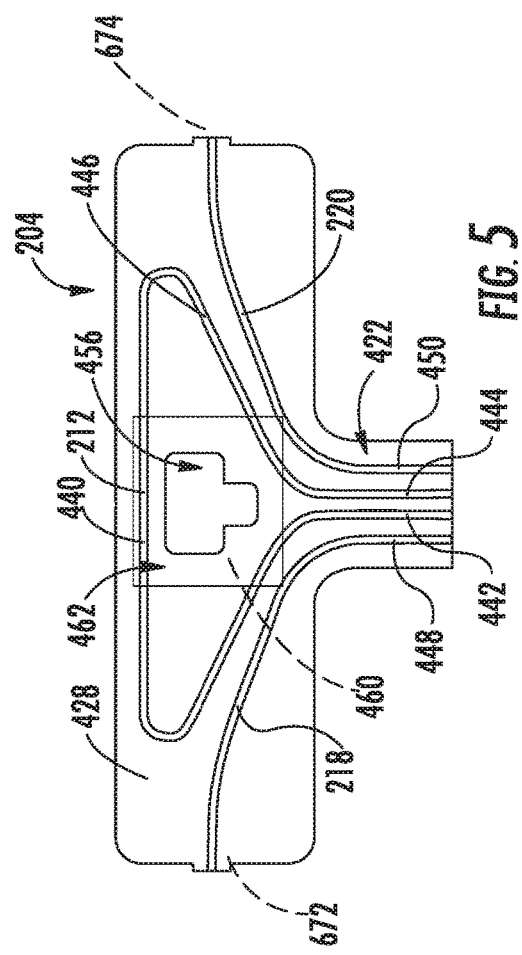
FIG. 5 is an elevation view similar to FIG. 4 with the sensors pads in fully folded positions.

Referring now to FIG. 5, the illustrative flexible substrate 204 is shown with the surface 428 facing upward and the sensor pads 430, 432 facing downward in the fully folded positions 672, 674. In the fully folded positions 672, 674, the sensor pads 430, 432 face in the same direction as the surface 658.

Figure 6:
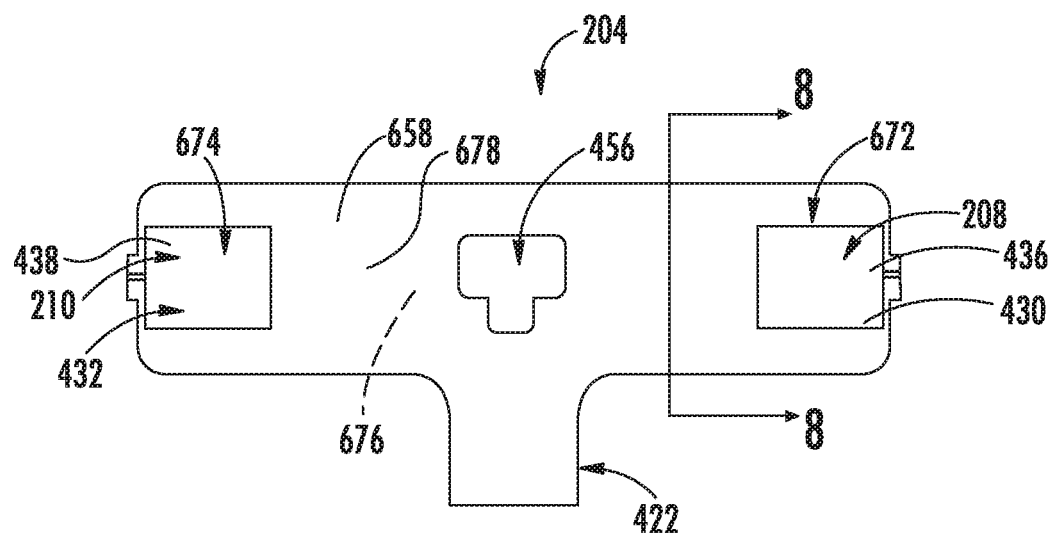
FIG. 6 is an elevation view of another side of the flexible substrate of FIG. 5 opposite the one side.

Referring now to FIG. 6, the illustrative flexible substrate 204 is shown with the surface 658 and the sensor pads 430, 432 facing upward and in the fully folded positions 672, 674 and the surface 428 facing downward. As discussed below, the surface 658 is configured for direct application to the skin of the subject 102 when the sensing patch system 100 is applied to the subject 102. Accordingly, the surface 658 illustratively includes an adhesive layer 676 configured to adhere to the subject 102 when the system 100 is applied to the subject 102. A cover 678 conceals the adhesive layer 676 to permit selective exposure of the adhesive layer 676 beneath the cover 678. When the cover 678 is removed and the sensor pads 430, 432 are folded to the fully folded positions 672, 674, the sensor pads 430, 432 are located on the surface 658 such that the pads 430, 432 adhere to the adhesive layer 676. Consequently, when the sensor pads 430, 432 are folded to the fully folded positions 672, 674 and the system 100 is applied to the subject 102, the sensor pads 430, 432 and the substrate sensors 208, 210 formed thereon contact the skin of the subject 102.

When the sensor pads 430, 432 are folded to the fully folded positions 672, 674 and the sensing patch system 100 is applied to the subject 102, electrical signals indicative of physiological characteristics of the subject 102 are produced by the electrodes 436, 438 of the substrate sensors 208, 210. Those signals are conducted by the substrate conductors 218, 220 to the node interface 422 and thereafter provided to the sensor node 214. In that way, the electrical signals are transmitted from the surface 658 that is in contact with the subject 102 to the surface 428 that is not in contact with the subject 102 without interaction with an intermediate device that is integrated into, or otherwise coupled to, the flexible substrate 204. Such intermediate devices may include, but are not limited to, printed circuit boards (PCBs) formed from polyimide or polyethylene terephthalate (PET), or mating electrical connectors, for example. In any case, exclusion of such an intermediate device may reduce the cost and fabrication complexity of the illustrative sensing patch system 100 compared to other configurations that employ such devices.

Figure 7:
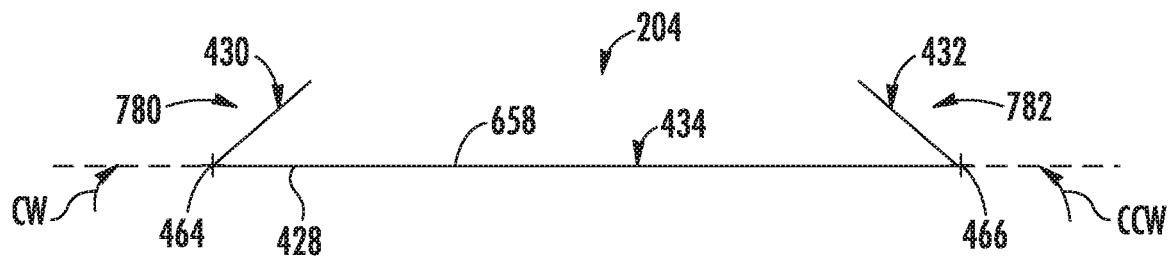
FIG. 7 is a top view of the flexible substrate of FIG. 4 with the sensor pads in partially folded positions.

Referring now to FIG. 7, the illustrative flexible substrate 204 is shown with the surface 658 facing upward, the surface 428 facing downward, and the sensor pads 430, 432 in partially folded positions 780, 782. The sensor pad 430 is folded relative to the body section 434 in a clockwise direction CW about the axis 464 to the partially folded position 780. In that sense, the partially folded position 780 represents an intermediate position of the pad 430 between the fully unfolded position 468 and the fully folded position 672 that is achieved when the pad 430 is moved from the position 468 toward the position 672. The sensor pad 432 is folded relative to the body section 434 in a counterclockwise direction CCW about the axis 466 to the partially folded position 782. In that sense, the partially folded position 782 represents an intermediate position of the pad 432 between the fully unfolded position 470 and the fully folded position 674 that is achieved when the pad 432 is moved from the position 470 toward the position 674.

Figure 8:
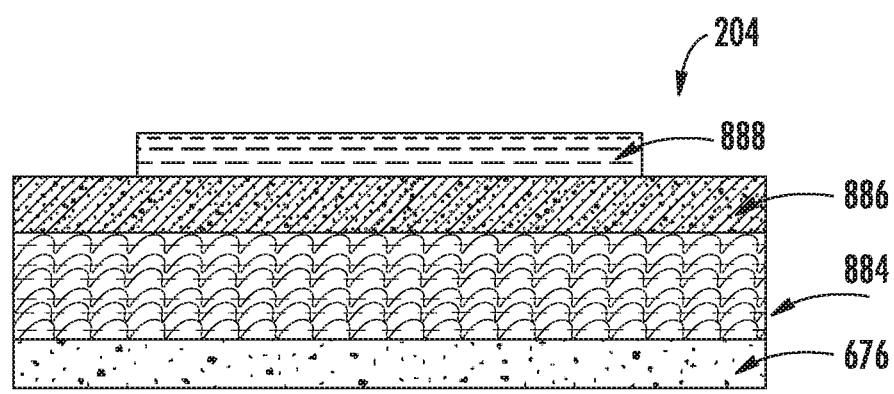
FIG. 8 is a sectional view of the flexible substrate taken about line 6-6 of FIG. 6.

Referring now to FIG. 8, the flexible substrate 204 illustratively includes a fabric base layer 884, a urethane layer 886 formed on and arranged above the fabric base layer 884, and an ink layer 888 formed on and arranged above the urethane layer 886. The adhesive layer 676 is formed on and arranged beneath the fabric base layer 884. An additional adhesive layer (not shown) that provides the adhesive region 460 may be formed on and arranged above the ink layer 888.

The illustrative fabric base layer 884 of the flexible substrate 204 is formed from a polymeric material. The illustrative fabric base layer 884 has a thickness of approximately 400 micrometers. In other embodiments, however, the fabric base layer 884 may be formed from another suitable material and have another suitable thickness. In any case, the layer 884 is configured to stretch in the horizontal direction H to a greater degree than in a vertical direction V that is substantially orthogonal to the horizontal direction H such that the layer 884 may be described as a two-way stretch fabric layer. That way, the layer 884 enables the body section 434 of the surface 428 to stretch in the direction H in response to movement of the subject 102 (e.g., stretching of the skin of the subject 102) parallel to the direction H when the sensing patch system 100 is applied to the subject 102. Such stretching facilitates measurement of variations in respirational activity by the substrate sensor 212 that may occur while the subject 102 is at rest or performing physical activity, for example. However, stretching of the body section 434 in the direction V in response to movement of the subject 102 parallel to the direction V is limited by the layer 884.

The illustrative urethane layer 886 of the flexible substrate 204 is formed from a thermoplastic urethane material. The illustrative urethane layer 886 has a thickness in the range of approximately 25 to 75 micrometers. In other embodiments, however, the layer 886 may be formed from another suitable material and have another suitable thickness. In any case, the urethane layer 886 is illustratively formed on the fabric base layer 884 by a heat press technique. However, in other embodiments, another suitable technique may be employed to form the urethane layer 886 on the fabric base layer 884.

The illustrative ink layer 888 of the flexible substrate 204 is formed from a conductive ink that includes one or more metallic materials, which may include conductive fabrics or conductive threads. In one example, the ink layer 888 is formed from a conductive ink that includes silver. The composition of the illustrative ink layer 888 may permit the electrodes 436, 438, the electrical trace 440, and the substrate conductors 218, 220, which are formed by the ink layer 888, to stretch to a greater degree than might otherwise be the case if those features were formed by a conductive ink having a different composition. The composition of the ink layer 888 may permit the electrodes 436, 438, the electrical trace 440, and the substrate conductors 218, 220 to stretch with the fabric base layer 884 to a greater degree than any stretching permitted by a conductive ink including copper materials, for example. In any case, the electrodes 436, 438, the electrical trace 440, and the substrate conductors 218, 220 are printed in conductive ink on the urethane layer 886 by a single print screen swipe such that those features are formed on a single layer, rather than on multiple layers and/or multiple surfaces. Printing those features on the urethane layer 886 by a single screen print swipe may reduce the cost and fabrication complexity of the illustrative sensing patch system 100 compared to other configurations that utilize multiple screen print swipes on multiple surfaces. The illustrative ink layer 888 of the flexible substrate 204 has a thickness of approximately 5 micrometers. In other embodiments, however, the ink layer 888 may have another suitable thickness.

The illustrative adhesive layer 676 of the flexible substrate 204 may include any adhesive capable of adhering the surface 658 to the skin of the subject 102. In the illustrative embodiment, the adhesive layer 676 includes a pressure-sensitive adhesive configured for contact with the skin of the subject 102 and capable of removal from the subject 102, such as a silicon adhesive, for example. In other embodiments, however, the adhesive layer 676 may include a drying adhesive, a contact adhesive, a hot adhesive, a one-part adhesive, a multi-part adhesive, a natural adhesive, and/or a synthetic adhesive. The illustrative adhesive layer 676 of the flexible substrate 204 has a thickness in the range of approximately 75 to 200 micrometers. In other embodiments, however, the adhesive layer 676 may have another suitable thickness.

Referring still to FIG. 8, the flexible substrate 204 is illustratively embodied as a disposable component that is configured for one-time usage in each of multiple applications. Because the sensing patch system 100 includes the flexible substrate 204 and the sensor node 214, which is configured for repeated usage in each of multiple applications as indicated above, the illustrative system 100 may be described as a semi-disposable, or semi-reusable, system.

Referring now to FIG. 9, the illustrative sensor node 214 includes a main body 990. The main body 990 houses and thereby supports circuitry and/or components used to control operation of the sensor node 214, as discussed in more detail below. The main body 990 includes a surface 992 and a surface 994 that is arranged opposite the surface 992. When the sensor node 214 is received by the cutout 456 of the flexible substrate 204, the surface 992 contacts the surface 428 of the flexible substrate 204, as further discussed below.

The illustrative sensor node 214 also includes node contacts 996 that are supported by the main body 990. The node contacts 996 illustratively include, or are otherwise embodied as, any devices capable of establishing electrical contact with the terminal ends 442, 444, 448, 450 located at the node interface 422 when the node interface 422 is received by the sensor node 214. In the illustrative embodiment, the node contacts 996 include four metallic, spring-biased contacts such as pogo pins. In other embodiments, however, the node contacts 996 may include another suitable number of contacts made from other suitable materials, such as machined or injection-molded plastic materials, for example. In any case, the node contacts 996 protrude from the main body 990 and are arranged for alignment with the terminal ends 442, 444, 448, 450 located at the node interface 422.

Figure 10:
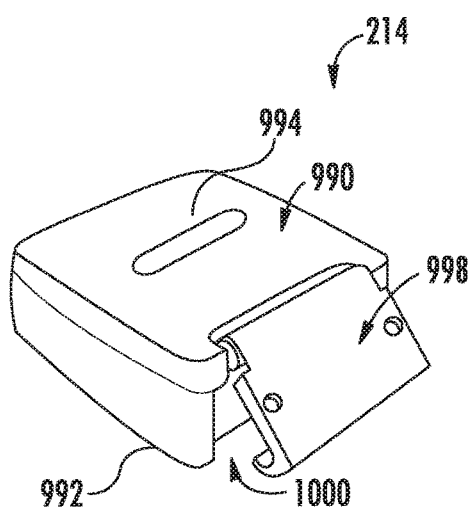
FIG. 10 is an assembled perspective view of the sensor node of FIG. 9 with a door of the sensor node arranged relative to a main body thereof in an open position.

Referring now to FIGS. 9 and 10, the illustrative sensor node 214 also includes a door or flap 998 that is pivotably coupled to the main body 990 in close proximity to the surface 994. More specifically, the door 998 is pivotable relative to the main body 990 between an open position 1000 and a closed position 1100. In the open position 1000, the door 998 permits the substrate interface 926 of the sensor node 214 to receive the node interface 422 of the flexible substrate 204. In the closed position 1100, after the substrate interface 926 is aligned with the node interface 422 as further discussed below, the door 998 secures electrical contact between the node contacts 996 and the terminal ends 442, 444, 448, 450.

Figure 11:
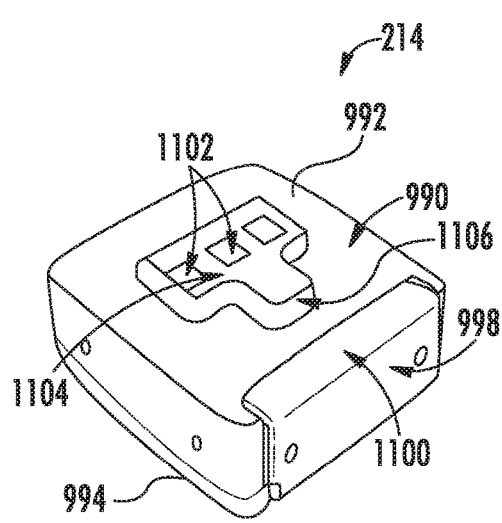
FIG. 11 is an assembled perspective view of the sensor node of FIG. 9 with the one side facing downward and the door arranged relative to the main body in a closed position.
Figure 12:
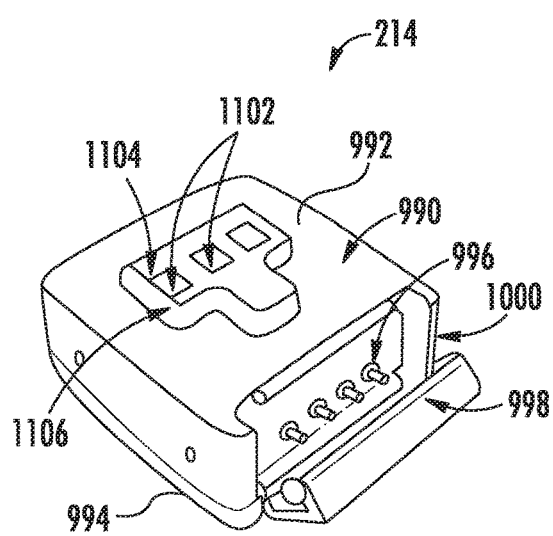
FIG. 12 is a perspective view of the sensor node similar to FIG. 11 with the door arranged relative to the main body in the open position.

Referring now to FIGS. 11 and 12, the illustrative sensor node 214 also includes node sensors 1102 and a generally T-shaped projection 1106. The node sensors 1102 are configured to provide node sensor data indicative of physiological characteristics of the subject 102. As discussed below, the node sensors 1102 may include reusable LEDs and photodiodes that sense blood flow and/or skin temperature of the subject 102. The node sensors 1102 each illustratively include a subject interface 1104. The projection 1106 illustratively extends outwardly away from the surface 992 of the main body 990, and the subject interface 1104 of each of the sensors 1102 is at least partially positioned in the projection 1106. As a result, when the sensor node 214 is received by the cutout 456 of the flexible substrate 204 and the sensing patch system 100 is applied to the subject 102, the projection 1106 and the subject interfaces 1104 extend outwardly from the cutout 456 to contact the subject 102.

When the door 998 is in the closed position 1100 shown in FIG. 11, the node contacts 996 are illustratively concealed. Conversely, when the door 998 is in the open position 1000 shown in FIG. 12, the node contacts 998 are illustratively exposed.

Figure 13:
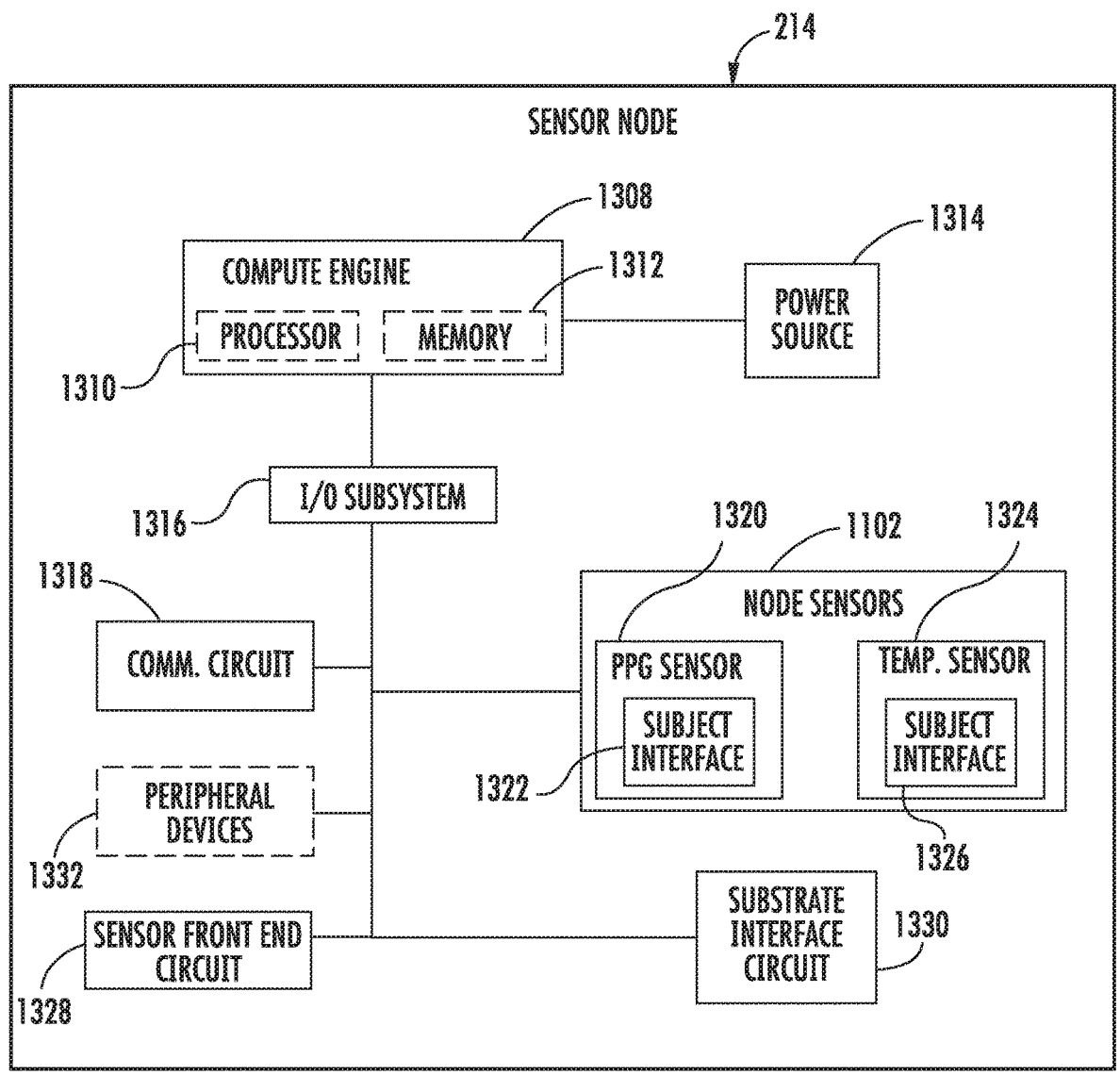
FIG. 13 a diagrammatic view of the sensor node of FIG. 9.

Referring now to FIG. 13, the illustrative sensor node 214 includes a compute engine 1308, a power source 1314, an input/output ("I/O") subsystem 1316, a communication circuit 1318, node sensors 1102, a sensor front-end circuit 1328, and a substrate interface circuit 1330. Of course, it should be appreciated that in other embodiments, the sensor node 214 may include other or additional components. Additionally, in some embodiments, one or more of the illustrative components may be incorporated in, or otherwise form a portion of, another component.

The illustrative compute engine 1308 may be embodied as any type of device or collection of devices capable of performing various compute functions. In some embodiments, the compute engine 1308 may be embodied as a single device such as an integrated circuit, an embedded system, a field-programmable-array (FPGA), a system-on-a-chip (SOC), or other integrated system or device. Additionally, in some embodiments, the compute engine 1308 includes, or is otherwise embodied as, a processor 1310 and memory 1312. The processor 1310 may be embodied as any type of processor capable of processing the sensor data provided by the substrate sensors 208, 210, 212 and/or the node sensors 1102 and communicating the processed sensor data to a remote device, among other things. For example, the processor 1310 may be embodied as a single or multi-core processor(s), digital signal processor, microcontroller, or other processor or processing/controlling circuit. Similarly, the memory 1312 may be embodied as any type of volatile or non-volatile memory or data storage capable of storing instructions for processing the sensor data provided by the substrate sensors 208, 210, 212 and/or the node sensors 1102 and communicating the processed sensor data to a remote device, among other things. In operation, the memory 1312 may store various data and software used during operation of the sensor node 214 such as operating systems, applications, programs, libraries, and drivers.

The illustrative power source 1314 may be embodied as any type of device capable of powering the compute engine 1308. In some embodiments, the power source 1314 may be embodied as an energy storage unit such as a primary battery, for example. Additionally, in some embodiments, the power source 1314 may be embodied as an energy storage unit such as a rechargeable battery, for example.

The illustrative compute engine 1308 is communicatively coupled to other components of the sensor node 214 via the I/O subsystem 1316, which may be embodied as circuitry and/or components to facilitate input/output operations with compute engine 1308 (e.g., with the processor 1310 and/or memory 1312) and other components of the sensor node 214. For example, the I/O subsystem 1316 may include, or otherwise be embodied as, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 1316 may be incorporated, along with the processor 1310, the memory 1312, and other components of the sensor node 214, into the compute engine 1308.

The illustrative communication circuit 1318 may be embodied as any type of communication circuit, device, or collection thereof, capable of enabling communications between the sensor node 214 and a remote device such that processed sensor data may be transmitted from the sensor node 214 to the remote device via a network. To do so, the communication circuit 1318 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

Node sensors 1102 illustratively include a photoplethysmogram (PPG) sensor 1320 having a subject interface 1322 and a temperature sensor 1324 having a subject interface 1326. The PPG sensor 1320 is illustratively embodied as any type of device, or collection of devices, capable of providing sensor data indicative of a volumetric measurement of an organ of the subject 102 based on light absorption. The sensor data provided by the PPG sensor 1320 may be indicative of cardiac and/or respiratory activity of the subject 102, for example. The temperature sensor 1324 is illustratively embodied as any type of device, or collection of devices, capable of providing sensor data indicative of the temperature of the subject 102. The sensor data provided by the temperature sensor 1324 may be indicative of temperature measured at the skin of the subject 102, for example. In other embodiments, however, the node sensors 1102 may include other suitable sensing devices.

The illustrative sensor front-end circuit 1328 may be embodied as circuitry and/or components capable of receiving the sensor data provided by the substrate sensors 208, 210, 212 and/or the node sensors 1102, amplifying the sensor data, and conditioning the sensor data in preparation for communicating the sensor data to a remote device. Control of the front-end circuit 1328 may be performed by the compute engine 1308 such that the receipt, amplification, and conditioning operations may be included in, or otherwise form a portion of, the processing operation performed by the compute engine 1308. In any case, the front-end circuit 1328 may include one or more signal amplifiers, such as analog signal amplifiers, for example, capable of amplifying the sensor data received from the substrate sensors 208, 210, 212 and/or the node sensors 1102. The front-end circuit 1328 may also include an alternating current-to-direct current (AC-DC) converter capable of converting analog sensor data to digitized signals which may be communicated to the remote device, as well as one or more filters capable of filtering the sensor data to generate filtered sensor data. The analog-to-digital conversion and filtering operations may be included in, or otherwise form a portion of, the conditioning operation discussed above.

The illustrative substrate interface circuit 1330 may be embodied as circuitry and/or components capable of receiving sensor data provided by the substrate sensors 208, 210, 212 to the substrate interface 926 of the sensor node 214 and providing the sensor data to the sensor front-end circuit 1328 for amplification and conditioning as discussed above. In some embodiments, the substrate interface circuit 1330 may include components capable of amplifying and conditioning the sensor data provided to the substrate interface 926 such that the sensor data need not be provided to the sensor front-end circuit 1328 for further amplification and conditioning. In any case, the node contacts 996 may be included in, or otherwise form a portion of, the substrate interface circuit 1330.

In some embodiments, the sensor node 214 may also include one or more peripheral devices 1332. The peripheral devices 1332 may include any number of additional peripheral or interface devices, such as other input/output devices, storage devices, and so forth. The particular devices included in the peripheral devices 1332 may depend on, for example, the type and/or configuration of the sensor node 214.

Figure 14:
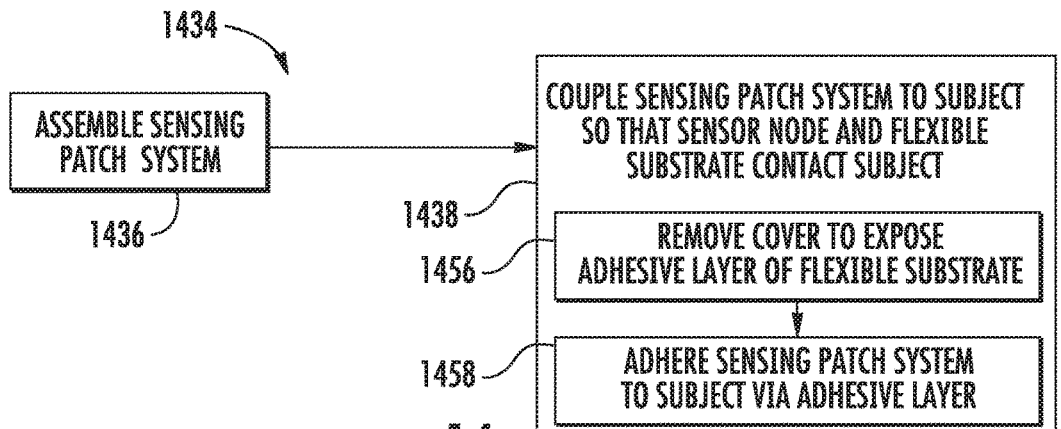
FIG. 14 is a diagrammatic view of at least one embodiment of a method of applying the sensing patch system of FIG. 1 to a subject.

Referring now to FIG. 14, a method 1434 of applying the illustrative sensing patch system 100 to the subject 102 is shown. As described in more detail below, the method 1434 includes assembling the sensing patch system 100 as indicated by block 1436. The method 1434 additionally includes coupling the sensing patch system 100 to the subject 102 such that the sensor node 214 and the flexible substrate 204 contact the subject 102 as indicated by block 1438. It should be appreciated that the method 1434 may be performed in a number of sequences other than the illustrative sequence of FIG. 14. Additionally, it should be appreciated that assembling the sensing patch system 100 as indicated by block 1436 may be performed in a number of sequences other than the sequence described below with reference to FIG. 15.

Figure 15:
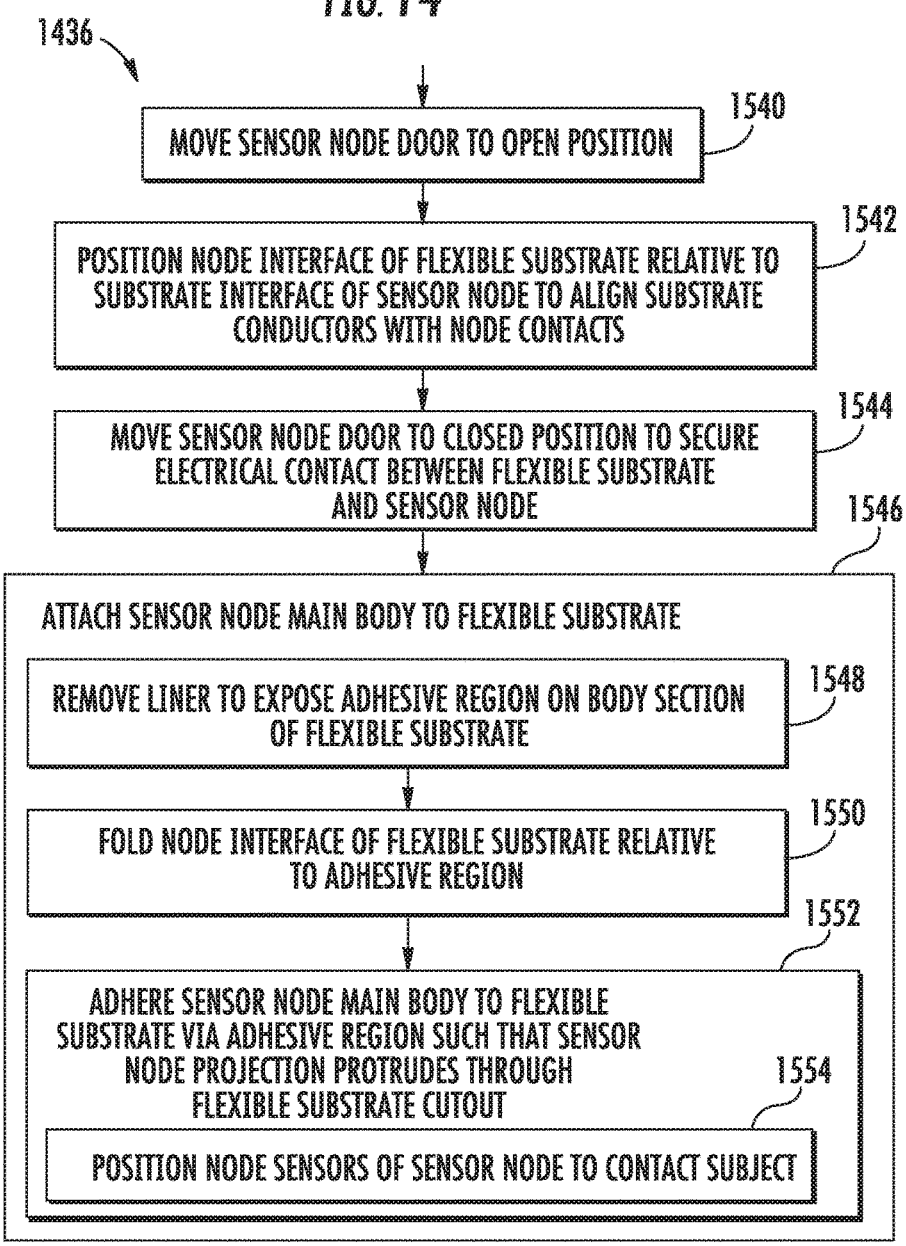
FIG. 15 is a diagrammatic view of at least one embodiment of a method of assembling the sensing patch system of FIG. 1.
Figure 16:
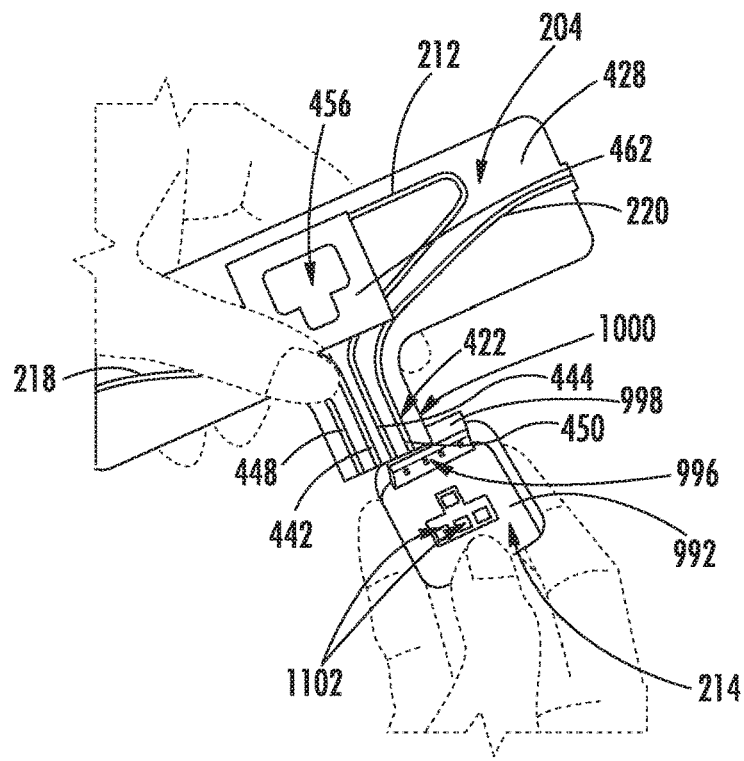
FIG. 16 is a perspective view of the sensing patch system with a substrate interface of the sensor node positioned in proximity to a node interface of the flexible substrate when assembling the sensing patch system by the method of FIG. 15.

Referring now to FIGS. 15 and 16, assembling the illustrative sensing patch system 100 as indicated by block 1436 begins with block 1540. In block 1540, the door 998 of the sensor node 214 is moved relative to the main body 990 of the sensor node 214 to the open position 1000. The substrate interface 926 of the sensor node 214, which includes the node contacts 996, is exposed when the door 998 is moved to the open position 1000, as best seen in FIG. 16.

Referring now to FIGS. 15 and 17, assembling the illustrative sensing patch system 100 as indicated by block 1436 proceeds from block 1540 to block 1542. In block 1542, the node interface 422 of the flexible substrate 204 is positioned relative to the exposed substrate interface 926 of the sensor node 214 to align the node interface 422 with the substrate interface 926. More specifically, as best seen in FIG. 17, the node interface 422 is positioned relative to the exposed substrate interface 926 to align the terminal ends 448, 450 of the substrate conductors 218, 220 and the terminal ends 442, 444 of the substrate sensor 212, which are located at the node interface 422, with the node contacts 996.

Referring now to FIGS. 15 and 18, assembling the illustrative sensing patch system 100 as indicated by block 1436 proceeds from block 1542 to block 1544. In block 1544, the door 998 of the sensor node 214 is moved to the closed position 1100 as shown in FIG. 18 such that the node interface 422 of the flexible substrate 204 is arranged between the substrate interface 926 of the sensor node 214 and the door 998. Consequently, movement of the door 998 to the closed position 1100 secures electrical contact between the terminal ends 442, 444, 448, 450 and the node contacts 996, thereby securing electrical contact between the flexible substrate 204 and the sensor node 214.

Figure 19:
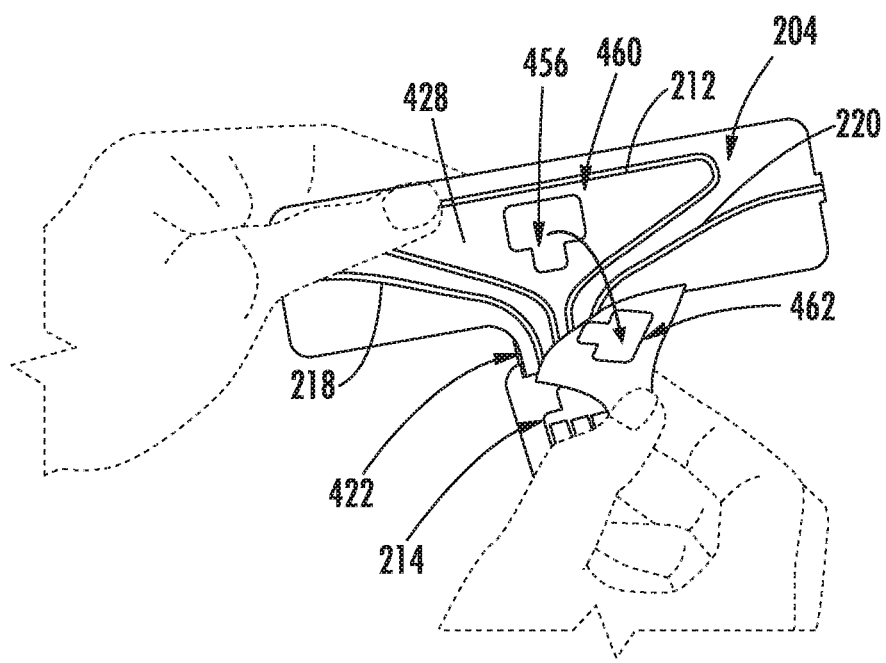
FIG. 19 is a perspective view of the sensing patch system with a cover of the flexible substrate removed to expose an adhesive layer thereof when assembling the sensing patch system by the method of FIG. 15.
Figure 20:
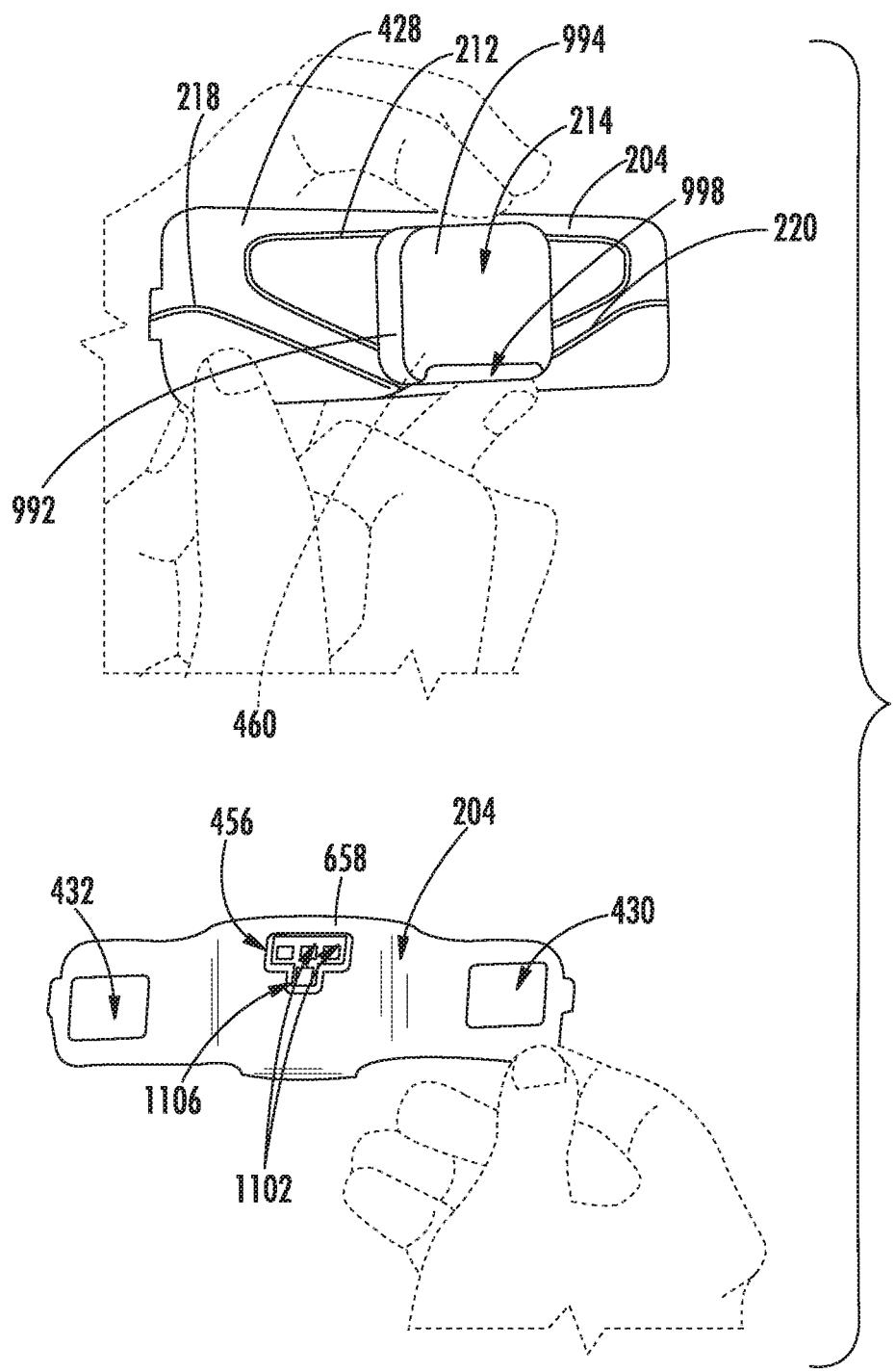
FIG. 20 is a perspective view of the sensing patch system with the sensor node adhered to the adhesive layer such that a projection thereof protrudes through a cutout of the flexible substrate when assembling the sensing patch system by the method of FIG. 15.

Referring now to FIGS. 15, 19, and 20, assembling the illustrative sensing patch system 100 as indicated by block 1436 proceeds from block 1544 to block 1546. In block 1546, the main body 990 of the sensor node 214 is attached to the flexible substrate 204. More specifically, the main body 990 is attached to the flexible substrate 204 such that the surface 992 of the main body 990 contacts the surface 428 of the flexible substrate 204. As discussed in more detail below, block 1546 includes sub-blocks 1548, 1550, and 1552.

Block 1546 includes sub-block 1548 as shown in FIG. 15. In sub-block 1548, the liner 462 of the flexible substrate 204 is removed to expose the adhesive region 460 formed on the body section 434 of the flexible substrate 204, as best seen in FIG. 19.

Block 1546 includes sub-block 1550 which follows sub-block 1548 in the illustrative sequence of FIG. 15. In sub-block 1550, the node interface 422 of the flexible substrate 204 is folded relative to the adhesive region 460 to arrange the surface 992 of the sensor node 214 in close proximity to the adhesive region 460, as best seen in FIG. 20.

Block 1546 includes sub-block 1552 which follows sub-block 1550 in the illustrative sequence of FIG. 15. In sub-block 1552, the surface 992 of the sensor node 214 is adhered to the flexible substrate 204 via the adhesive region 460. More specifically, the surface 992 is adhered to the flexible substrate 204 via the adhesive region 460 such that the projection 1106 of the sensor node 214 protrudes through the cutout 456 of the flexible substrate 204, as best seen in FIG. 20. In some embodiments, sub-block 1552 may include sub-block 1554. In sub-block 1554, the node sensors 1102 of the sensor node 214 are positioned to contact the subject 102, as suggested by FIG. 20.

Returning now to FIG. 14, coupling the sensing patch system 100 to the subject 102 such that the sensor node 214 and the flexible substrate 204 contact the subject 102 as indicated by block 1438 includes sub-blocks 1456 and 1458. In sub-block 1456, the cover 678 is removed to expose the adhesive layer 676 of the surface 658 of the flexible substrate 204. In some embodiments, sub-block 1456 may include folding the sensor pads 430, 432 onto the exposed adhesive layer 676 so that the pads 430, 432 are in the fully folded positions 672, 674 on the surface 658.

In sub-block 1458, the assembled sensing patch system 100 is adhered to the subject 102 via the adhesive layer 676. When the sensing patch system 100 is adhered to the subject 102, the surface 658 of the flexible substrate 204 and the projection 1106 of the sensor node 214 contact the subject 102.

Figure 21:
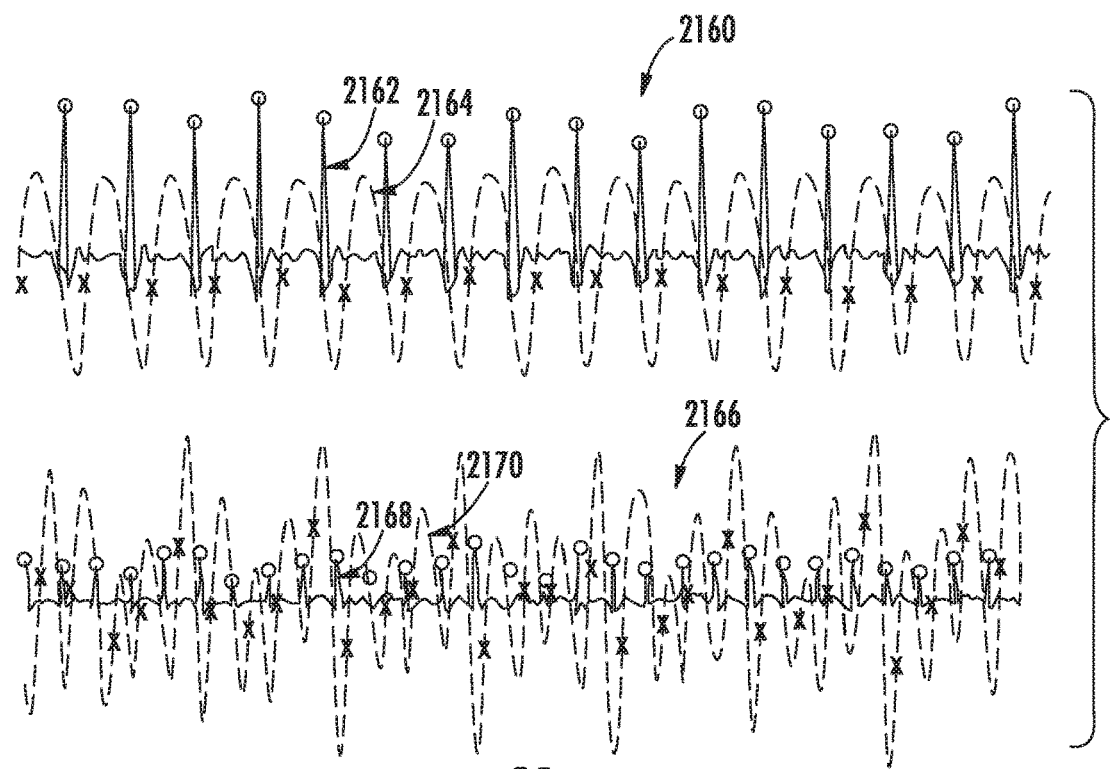
FIG. 21 is a graphical depiction of physiological activity sensed by a sensing patch system that is applied to a human subject.

Referring now to FIG. 21, illustrative subject data 2160 indicative of physiological characteristics measured at rest and illustrative subject data 2166 indicative of physiological characteristics measured during physical activity are shown. Both the subject data 2160 and the subject data 2166 illustratively include actual data provided in real-time by a sensing patch system 100 applied to a human subject 102.

The subject data 2160 illustratively indicates physiological characteristics of the subject 102 measured when the heart rate of the subject 102 is approximately 80 beats per minute, which may correspond to an at-rest condition of the subject 102. The subject data 2166 illustratively indicates physiological characteristics of the subject 102 measured when the heart rate of the subject 102 is approximately 180 beats per minute, which may correspond to a peak exercise condition of the subject 102. The subject data 2160 and the subject data 2166 are displayed in FIG. 21 to demonstrate signal quality during different conditions, such as during the at-rest and peak exercise conditions, for example. It should be appreciated that the signal quality demonstrated by the subject data 2160, 2166 may facilitate diastolic and systolic blood pressure measurements, as discussed below.

The subject data 2160 illustratively includes ECG data 2162 and PPG data 2164. The ECG data 2162 may illustratively indicate cardiac and/or respiratory activity of the subject 102 sensed by the electrocardiogram electrodes 436, 438 of the respective substrate sensors 208, 210, for example. The PPG data 2164 may illustratively indicate cardiac and/or respiratory activity of the subject 102 sensed by the photoplethysmogram sensor 1320 of the sensor node 214, for example.

The subject data 2166 illustratively includes ECG data 2168 and PPG data 2170. The ECG data 2168 may illustratively indicate cardiac and/or respiratory activity of the subject 102 sensed by the electrocardiogram electrodes 436, 438 of the respective substrate sensors 208, 210, for example. The PPG data 2170 may illustratively indicate cardiac and/or respiratory activity of the subject 102 sensed by the photoplethysmogram sensor 1320 of the sensor node 214, for example.

Figure 22:
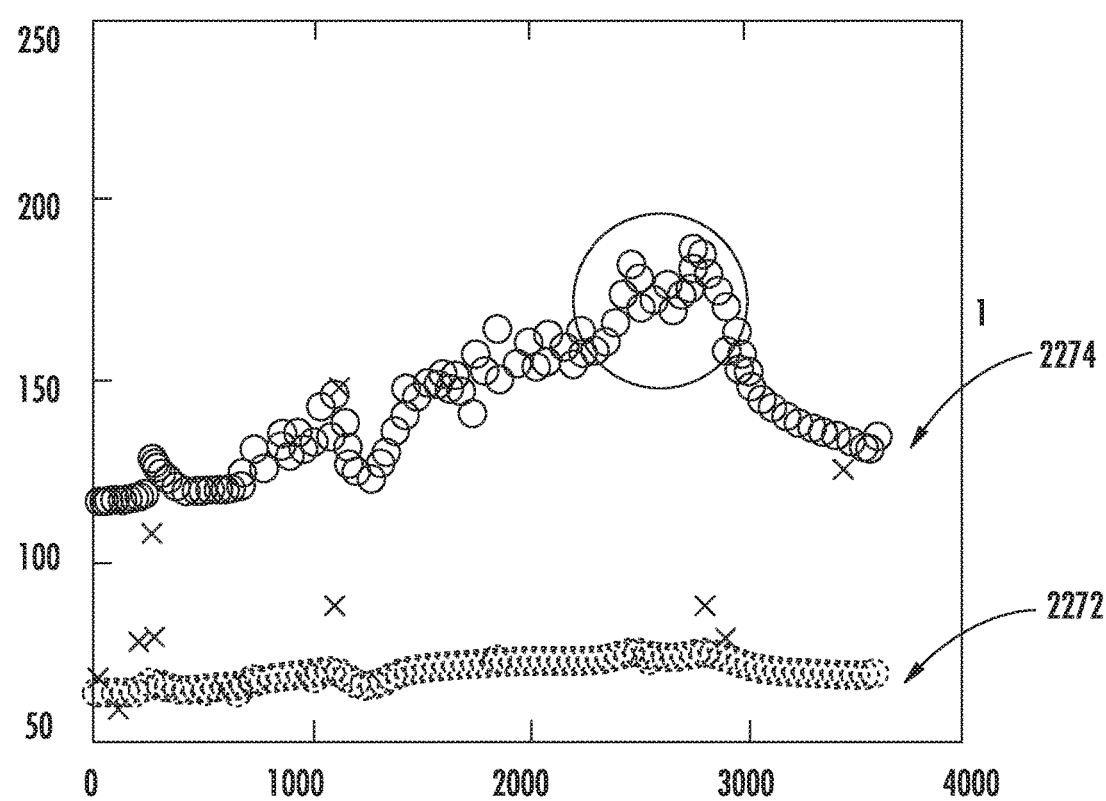
FIG. 22 is a graphical depiction of blood pressure trends associated with the physiological activity of FIG. 21.

Referring now to FIGS. 21 and 22, the ECG data 2162 and the PPG data 2164 overlap with one another, and the ECG data 2168 and the PPG data 2170 overlap with one another. The signal quality of the overlapping ECG data 2162 and the PPG data 2164 may illustratively facilitate reliable estimation of a blood pressure trend 2272 of the subject 102, as best seen in FIG. 22. For example, the blood pressure trend 2272 may correspond to a diastolic blood pressure trend. The signal quality of the overlapping ECG data 2168 and the PPG data 2170 may illustratively facilitate reliable estimation of a blood pressure trend 2274 of the subject 102, as best seen in FIG. 22. For example, the blood pressure trend 2274 may correspond to a systolic blood pressure trend. The horizontal scale of the graph shown in FIG. 22 may correspond to time measured in minutes or seconds, for example. The vertical scale of the graph shown in FIG. 22 may correspond to blood pressure measured in mmHg, for example. The ends of the blood pressure trends 2272, 2274 (i.e., near the beginning and ending of the time-based horizontal scale) may be associated with at-rest conditions of the subject 102, whereas the middle of the blood pressure trends 2272, 2274 (i.e., toward the middle of the time-based horizontal scale) may be associated with a peak exercise condition of the subject 102.

EXAMPLES

Illustrative examples of the technologies disclosed herein are provided below. An embodiment of the technologies may include any one or more, and any combination of, the examples described below.

Example 1 includes a sensing patch system comprising a flexible substrate comprising (i) one or more substrate sensors configured to provide sensor data, (ii) one or more substrate conductors, wherein each substrate conductor is electrically coupled to a corresponding substrate sensor to conduct the sensor data provided by the corresponding substrate sensor, and (iii) a node interface, wherein each of the substrate conductors includes a terminal end located at the node interface; and a sensor node comprising a substrate interface configured to receive the node interface of the flexible substrate, wherein the sensor node establishes electrical contact with each of the terminal ends of the substrate conductors when the node interface is received by the substrate interface, the sensor node further configured to receive the sensor data provided by the sensors, process the sensor data, and communicate the processed sensor data to a remote device.

Example 2 includes the subject matter of Example 1, and wherein (i) the flexible substrate includes a first surface that is configured to contact a subject and a second surface that faces away from the first surface and (ii) the substrate conductors are formed on the second surface.

Example 3 includes the subject matter of any of Examples 1 and 2, and wherein at least a portion of at least one substrate conductor formed on the second surface is non-insulated.

Example 4 includes the subject matter of any of Examples 1-3, and wherein (i) the one or more substrate sensors include a first electrode formed on a first sensor pad of the second surface and a second electrode formed on a second sensor pad of the second surface and (ii) each of the first and second sensor pads are foldable onto the first surface such that the first and second electrodes face in the same direction as the first surface.

Example 5 includes the subject matter of any of Examples 1-4, and wherein the first surface of the flexible substrate includes an adhesive layer configured to adhere to the subject when the sensing patch system is applied to the subject and each of the first and second sensor pads are adhered to the adhesive layer when folded onto the first surface.

Example 6 includes the subject matter of any of Examples 1-5, and wherein the one or more substrate conductors and the one or more substrate sensors are formed on the second surface by a single screen print swipe.

Example 7 includes the subject matter of any of Examples 1-6, and wherein (i) the flexible substrate includes a cutout extending through the first and second surfaces and (ii) the sensor node is configured to be received by the cutout such that the sensor node directly contacts the subject when the sensing patch system is applied to the subject.

Example 8 includes the subject matter of any of Examples 1-7, and wherein the sensor node contacts the second surface when received in the cutout of the flexible substrate.

Example 9 includes the subject matter of any of Examples 1-8, and wherein (i) an adhesive region is formed on the second surface and (ii) the sensor node adheres to the adhesive region when received by the cutout of the flexible substrate.

Example 10 includes the subject matter of any of Examples 1-9, and wherein the sensor node is removable from the adhesive region.

Example 11 includes the subject matter of any of Examples 1-10, and wherein the adhesive region is formed around the cutout of the flexible substrate.

Example 12 includes the subject matter of any of Examples 1-11, and wherein (i) the one or more substrate sensors include a third sensor and (ii) the third sensor includes an electrical trace that extends around the cutout of the flexible substrate.

Example 13 includes the subject matter of any of Examples 1-12, and wherein the third sensor provides a breathing sensor configured to provide data indicative of respirational activity of the subject.

Example 14 includes the subject matter of any of Examples 1-13, and wherein the sensor node includes (i) at least one node sensor configured to provide node sensor data and (ii) the at least one node sensor includes a subject interface that extends outwardly from the cutout of the flexible substrate when the sensor node is received by the cutout of the flexible substrate.

Example 15 includes the subject matter of any of Examples 1-14, and wherein (i) the sensor node includes a main body and a projection that extends outwardly from the main body and (ii) the subject interface of the at least one node sensor is positioned at least partially in the projection to contact the subject when the sensor node is received by the cutout of the flexible substrate and the sensing patch system is applied to the subject.

Example 16 includes the subject matter of any of Examples 1-15, and wherein the sensor node includes a door that is pivotable relative to the main body between (i) an open position to permit the substrate interface of the sensor node to receive the node interface of the flexible substrate and (ii) a closed position to secure electrical contact between node contacts of the node sensor and each of the terminal ends of the substrate conductors.

Example 17 includes the subject matter of any of Examples 1-16, and wherein (i) the flexible substrate is configured for one-time usage in each of a plurality of applications and (ii) the sensor node is configured for repeated usage in each of the plurality of applications.

Example 18 includes the subject matter of any of Examples 1-17, and wherein the sensor node includes (i) a compute engine to process the sensor data and (ii) a communication circuit to transmit the processed sensor data to the remote device.

Example 19 includes a flexible substrate for a sensing patch system, the flexible substrate comprising a first surface configured to contact a subject; a second surface that faces away from the first surface; and one or more substrate sensors formed on the second surface that are configured to provide sensor data, wherein (i) the one or more substrate sensors include a first electrode formed on a first sensor pad of the second surface and a second electrode formed on a second sensor pad of the second surface and (ii) each of the first and second sensor pads are foldable onto the first surface such that the first and second electrodes face in the same direction as the first surface.

Example 20 includes the subject matter of Example 19, and further including one or more substrate conductors formed on the second surface, wherein (i) each substrate conductor is electrically coupled to a corresponding substrate sensor to conduct the sensor data provided by the corresponding substrate sensor and (ii) at least a portion of at least one substrate conductor is non-insulated.

Example 21 includes the subject matter of any of Examples 19 and 20, and wherein (i) the first surface includes an adhesive layer configured to adhere to the subject when the flexible substrate is applied to the subject and (ii) each of the first and second sensor pads are adhered to the adhesive layer when folded onto the first surface.

Example 22 includes the subject matter of any of Examples 19-21, and wherein the one or more substrate sensors and the one or more substrate conductors are formed on the second surface by a single screen print swipe.

Example 23 includes the subject matter of any of Examples 19-22, and wherein the flexible substrate includes a cutout extending through the first and second surfaces that is sized to receive a sensor node of the sensing patch system.

Example 24 includes the subject matter of any of Examples 19-23, and wherein (i) an adhesive region is formed on the second surface and (ii) the adhesive region is provided to adhere the sensor node to the second surface when the cutout receives the sensor node.

Example 25 includes the subject matter of any of Examples 19-24, and wherein the adhesive region is formed around the cutout.

Example 26 includes the subject matter of any of Examples 19-25, and wherein (i) the one or more substrate sensors include a third sensor and (ii) the third sensor includes an electrical trace that extends around the cutout.

Example 27 includes the subject matter of any of Examples 19-26, and wherein the third sensor provides a breathing sensor configured to provide data indicative of respirational activity of the subject.

Example 28 includes the subject matter of any of Examples 19-27, and wherein the flexible substrate is configured for one-time usage in each of a plurality of applications.

Example 29 includes a sensor node for a sensing patch system, the sensor node comprising a main body; node contacts supported by the main body; and a door that is pivotable relative to the main body between (i) an open position to permit a substrate interface of the sensor node to receive a flexible substrate of the sensing patch system and (ii) a closed position to secure electrical contact between the node contacts and the flexible substrate.

Example 30 includes the subject matter of Example 29, and further including at least one node sensor configured to provide node sensor data, wherein the at least one node sensor includes a subject interface.

Example 31 includes the subject matter of any of Examples 29 and 30, and further including a projection that extends outwardly from the main body, wherein the subject interface is positioned at least partially in the projection to contact a subject when the sensor node is applied to the subject.

Example 32 includes the subject matter of any of Examples 29-31, and wherein the sensor node is configured for repeated usage in each of a plurality of applications such that the at least one node sensor is configured for repeated usage in each of the plurality of applications.

Example 33 includes the subject matter of any of Examples 29-32, and further including (i) a compute engine to process sensor data provided by the flexible substrate and (ii) a communication circuit to transmit the processed sensor data to a remote device.

Example 34 includes a method of assembling a sensing patch system, the sensing patch system including (i) a flexible substrate and (ii) a sensor node, the method comprising moving a door of the sensor node relative to a main body of the sensor node to an open position to expose a substrate interface of the sensor node; positioning a node interface of the flexible substrate relative to the exposed substrate interface such that the node interface is aligned with the substrate interface; moving the door to a closed position such that the node interface is arranged between the substrate interface and the door to secure electrical contact between the flexible substrate and the sensor node; and attaching the main body of the sensor node to the flexible substrate.

Example 35 includes the subject matter of Example 34, and wherein attaching the main body of the sensor node to the flexible substrate further comprises removing a liner to expose an adhesive region provided on the flexible substrate that is spaced from the node interface; and folding the node interface relative to the adhesive region to arrange the main body of the sensor node in close proximity to the adhesive region.

Example 36 includes the subject matter of any of Examples 34 and 35, and wherein attaching the main body of the sensor node to the flexible substrate further comprises adhering the main body of the sensor node to the flexible substrate via the adhesive region such that a projection of the sensor node that extends outwardly from the main body protrudes through a cutout formed in the flexible substrate.

Example 37 includes the subject matter of any of Examples 34-36, and wherein adhering the main body of the sensor node to the flexible substrate via the adhesive region comprises positioning at least one node sensor of the sensor node that is partially disposed in the projection to contact a subject.

Example 38 includes a method of applying a sensing patch system to a subject, the sensing patch system including (i) a flexible substrate and (ii) a sensor node, the method comprising assembling the sensing patch system, and coupling the sensing patch system to the subject such that the sensor node and the flexible substrate contact the subject.

Example 39 includes the subject matter of Example 38, and wherein assembling the sensing patch system comprises moving a door of the sensor node relative to a main body of the sensor node to an open position to expose a substrate interface of the sensor node; positioning a node interface of the flexible substrate relative to the exposed substrate interface such that the node interface is aligned with the substrate interface; moving the door to a closed position such that the node interface is arranged between the substrate interface and the door to secure electrical contact between the flexible substrate and the sensor node; and attaching the main body of the sensor node to the flexible substrate.

Example 40 includes the subject matter of any of Examples 38 and 39, and wherein attaching the main body of the sensor node to the flexible substrate further comprises removing a liner to expose an adhesive region provided on the flexible substrate that is spaced from the node interface; and folding the node interface relative to the adhesive region to arrange the main body of the sensor node in close proximity to the adhesive region.

Example 41 includes the subject matter of any of Examples 38-40, and wherein attaching the main body of the sensor node to the flexible substrate further comprises adhering the main body of the sensor node to the flexible substrate via the adhesive region such that a projection of the sensor node that extends outwardly from the main body protrudes through a cutout formed in the flexible substrate.

Example 42 includes the subject matter of any of Examples 38-41, and wherein coupling the sensing patch system to the subject comprises contacting (i) the projection with the subject and (ii) a surface of the flexible substrate that faces away from the main body of the sensor node with the subject.

The invention claimed is:

1. A sensing patch system comprising:
a flexible substrate comprising (i) one or more substrate sensors configured to provide sensor data, (ii) one or more substrate conductors, wherein each substrate conductor is electrically coupled to a corresponding substrate sensor to conduct the sensor data provided by the corresponding substrate sensor, and (iii) a node interface, wherein each of the substrate conductors includes a terminal end located at the node interface; and a sensor node comprising a main body having a door and a substrate interface configured to receive the node interface of the flexible substrate, wherein the sensor node establishes electrical contact with each of the terminal ends of the substrate conductors when the node interface is received by the substrate interface, wherein the door of the sensor node is pivotable relative to the main body between (i) an open position to permit the substrate interface of the sensor node to receive the node interface of the flexible substrate and (ii) a closed position to secure electrical contact between node contacts of the node sensor and each of the terminal ends of the substrate conductors, and wherein the sensor node is further configured to receive the sensor data provided by the sensors, process the sensor data, and communicate the processed sensor data to a remote device.

2. The sensing patch system of claim 1, wherein (i) the flexible substrate includes a first surface that is configured to contact a subject and a second surface that faces away from the first surface and (ii) the substrate conductors are formed on the second surface.

3. The sensing patch system of claim 2, wherein (i) the one or more substrate sensors include a first electrode formed on a first sensor pad of the second surface and a second electrode formed on a second sensor pad of the second surface and (ii) each of the first and second sensor pads are foldable onto the first surface such that the first and second electrodes face in the same direction as the first surface.

4. The sensing patch system of claim 3, wherein the first surface of the flexible substrate includes an adhesive layer configured to adhere to the subject when the sensing patch system is applied to the subject and each of the first and second sensor pads are adhered to the adhesive layer when folded onto the first surface.

5. The sensing patch system of claim 3, wherein (i) the flexible substrate includes a cutout extending through the first and second surfaces and (ii) the sensor node is configured to be received by the cutout such that the sensor node directly contacts the subject when the sensing patch system is applied to the subject.

6. The sensing patch system of claim 5, wherein (i) an adhesive region is formed on the second surface and (ii) the sensor node adheres to the adhesive region when received by the cutout of the flexible substrate.

7. The sensing patch system of claim 6, wherein the adhesive region is formed around the cutout of the flexible substrate.

8. The sensing patch system of claim 5, wherein (i) the one or more substrate sensors include a third sensor and (ii) the third sensor includes an electrical trace that extends around the cutout of the flexible substrate.

9. The sensing patch system of claim 8, wherein the third sensor provides a breathing sensor configured to provide data indicative of respirational activity of the subject.

10. The sensing patch system of claim 5, wherein the sensor node includes (i) at least one node sensor configured to provide node sensor data and (ii) the at least one node sensor includes a subject interface that extends outwardly from the cutout of the flexible substrate when the sensor node is received by the cutout of the flexible substrate.

11. The sensing patch system of claim 10, wherein (i) the sensor node a projection that extends outwardly from the main body and (ii) the subject interface of the at least one node sensor is positioned at least partially in the projection to contact the subject when the sensor node is received by the cutout of the flexible substrate and the sensing patch system is applied to the subject.

* * * * *